(12) United States Patent
Tirtowidjojo et al.

(10) Patent No.: US 9,475,740 B2
(45) Date of Patent: Oct. 25, 2016

(54) PROCESS FOR THE PRODUCTION OF CHLORINATED PROPENES

(71) Applicant: Blue Cube IP LLC, Midland, MI (US)

(72) Inventors: Max M. Tirtowidjojo, Lake Jackson, TX (US); David S. Laitar, Midland, MI (US); Barry B. Fish, Lake Jackson, TX (US); William J. Kruper, Jr., Sanford, MI (US)

(73) Assignee: BLUE CUBE IP LLC, Midland, MI (US)

( * ) Notice: Subject to any disclaimer, the term of this patent is extended or adjusted under 35 U.S.C. 154(b) by 0 days.

(21) Appl. No.: 14/653,526

(22) PCT Filed: Dec. 17, 2013

(86) PCT No.: PCT/US2013/075863
§ 371 (c)(1),
(2) Date: Jun. 18, 2015

(87) PCT Pub. No.: WO2014/100039
PCT Pub. Date: Jun. 26, 2014

(65) Prior Publication Data
US 2015/0344387 A1 Dec. 3, 2015

Related U.S. Application Data

(60) Provisional application No. 61/739,341, filed on Dec. 19, 2012.

(51) Int. Cl.
C07C 17/25 (2006.01)

(52) U.S. Cl.
CPC .................................. C07C 17/25 (2013.01)

(58) Field of Classification Search
CPC ..................................................... C07C 17/25
See application file for complete search history.

(56) References Cited

U.S. PATENT DOCUMENTS

| | | |
|---|---|---|
| 2,119,484 A | 5/1938 | Levine et al. |
| 2,179,378 A | 11/1939 | Metzger |
| 2,207,193 A | 7/1940 | Groll |
| 2,299,441 A | 10/1942 | Vaughan et al. |
| 2,302,228 A | 11/1942 | Kharasch et al. |
| 2,370,342 A | 2/1945 | Zellner |
| 2,378,859 A | 6/1945 | Martin |
| 2,435,983 A | 2/1948 | Schmerling |
| 2,449,286 A | 9/1948 | Fairbairn |
| 2,588,867 A | 3/1952 | Morris |
| 2,630,461 A | 3/1953 | Sachsse et al. |
| 2,688,592 A | 9/1954 | Skeeters |
| 2,762,611 A | 9/1956 | Monroe |
| 2,765,359 A | 10/1956 | Pichler et al. |
| 2,964,579 A | 12/1960 | Weller et al. |
| 2,973,393 A | 2/1961 | Monroe |
| 3,000,980 A | 9/1961 | Asadorian |
| 3,094,567 A | 6/1963 | Eaker |
| 3,112,988 A | 12/1963 | Coldren et al. |
| 3,444,263 A | 5/1969 | Fernald |
| 3,446,859 A | 5/1969 | Weil |
| 3,502,734 A | 3/1970 | Baird |
| 3,525,595 A | 8/1970 | Zirngibl et al. |
| 3,551,512 A | 12/1970 | Loeffler |
| 3,558,438 A | 1/1971 | Schoenbeck |
| 3,651,019 A | 3/1972 | Asscher |
| 3,676,508 A | 7/1972 | Krekeler |
| 3,819,731 A | 6/1974 | Pitt |
| 3,823,195 A | 7/1974 | Smith |
| 3,872,664 A | 3/1975 | Lohmann |
| 3,914,167 A | 10/1975 | Ivy |
| 3,920,757 A | 11/1975 | Watson |
| 3,926,758 A | 12/1975 | Smith |
| 3,948,858 A | 4/1976 | Wiersum |
| 3,954,410 A | 5/1976 | Pohl et al. |
| 4,038,372 A | 7/1977 | Colli |
| 4,046,656 A | 9/1977 | Davis et al. |
| 4,051,182 A | 9/1977 | Pitt |
| 4,319,062 A | 3/1982 | Boozalis et al. |
| 4,513,154 A | 4/1985 | Kurtz |
| 4,535,194 A | 8/1985 | Woodard |
| 4,614,572 A | 9/1986 | Holbrook |
| 4,644,907 A | 2/1987 | Hunter |
| 4,650,914 A | 3/1987 | Woodard |
| 4,661,648 A | 4/1987 | Franklin |
| 4,702,809 A | 10/1987 | Mueller |
| 4,714,792 A | 12/1987 | Muller et al. |

(Continued)

FOREIGN PATENT DOCUMENTS

| CH | 609022 | 6/1974 |
|---|---|---|
| CN | 101215220 | 7/2008 |

(Continued)

OTHER PUBLICATIONS

Michigan Technological Univ., "Free-Radical Chlorination with Sulfuryl Chloride", Nov. 15, 2001, 1-7.
Bai, et al., "Isomerization of Tetrachloropropene to Promote Utilization Ratio of Triallate Raw Materials", Petrochemical Technology & Application, 2007, 25(1).
Chai, et al., "Study of Preparation of 1,1,1,3-tetrachloropropane", Zhejiang Chemical Industry, 2010, pp. 1-3, 41(5).
Cristiano, et al., "Tetraalkylphosphonium Trihalides. Room Temperature Ionic Liquids As Halogenation Reagents", J. Org. Chem., 2009, pp. 9027-9033, 74.
Evstigneev, et al., "Initiated Chlorination of Tetrachloropropane", Khim. Prom., 1984, pp. 393-394, 16(7).

(Continued)

Primary Examiner — Shailendra Kumar
(74) Attorney, Agent, or Firm — Polsinelli PC (57) ABSTRACT

Processes for the production of chlorinated propenes are provided. The present processes make use of 1,2-dichloropropane, a by-product in the production of chlorohydrin, as a low cost starting material. 1,1,1,2,2-pentachloropropane produced by the process is subjected to catalytic dehydrochlorination and build-up of the same within the process is avoided.

11 Claims, 4 Drawing Sheets

(56) References Cited

U.S. PATENT DOCUMENTS

| | | |
|---|---|---|
| 4,716,255 A | 12/1987 | Mueller |
| 4,726,686 A | 2/1988 | Wolf |
| 4,727,181 A | 2/1988 | Kruper |
| 4,849,554 A | 7/1989 | Cresswell et al. |
| 4,894,205 A | 1/1990 | Westerman |
| 4,902,393 A | 2/1990 | Muller |
| 4,999,102 A | 3/1991 | Cox |
| 5,057,634 A | 10/1991 | Webster |
| 5,132,473 A | 7/1992 | Furutaka |
| 5,171,899 A | 12/1992 | Furutaka |
| 5,178,844 A | 1/1993 | Carter et al. |
| 5,246,903 A | 9/1993 | Harley |
| 5,254,771 A | 10/1993 | Cremer |
| 5,254,772 A | 10/1993 | Dukat |
| 5,254,788 A | 10/1993 | Gartside |
| 5,262,575 A | 11/1993 | Dianis |
| 5,315,044 A | 5/1994 | Furutaka |
| 5,367,105 A | 11/1994 | Miyazaki et al. |
| 5,414,166 A | 5/1995 | Kim |
| 5,504,266 A | 4/1996 | Tirtowidjojo et al. |
| 5,684,219 A | 11/1997 | Boyce |
| 5,689,020 A | 11/1997 | Boyce |
| 5,811,605 A | 9/1998 | Tang |
| 5,895,825 A | 4/1999 | Elsheikh |
| 5,986,151 A | 11/1999 | Van Der Puy |
| 6,111,150 A | 8/2000 | Sakyu |
| 6,118,018 A | 9/2000 | Savidakis |
| 6,160,187 A | 12/2000 | Strickler |
| 6,187,976 B1 | 2/2001 | Van Der Puy |
| 6,229,057 B1 | 5/2001 | Jackson et al. |
| 6,235,951 B1 | 5/2001 | Sakyu et al. |
| 6,472,573 B1 | 10/2002 | Yamamoto |
| 6,518,467 B2 | 2/2003 | Tung et al. |
| 6,538,167 B1 | 3/2003 | Brown |
| 6,545,176 B1 | 4/2003 | Tsay |
| 6,551,469 B1 | 4/2003 | Nair |
| 6,610,177 B2 | 8/2003 | Tsay |
| 6,613,127 B1 | 9/2003 | Galloway |
| 6,683,216 B1 | 1/2004 | Zoeller |
| 6,825,383 B1 | 11/2004 | Dewkar |
| 6,924,403 B2 | 8/2005 | Barnes et al. |
| 6,958,135 B1 | 10/2005 | Filippi |
| 7,117,934 B2 | 10/2006 | Lomax |
| 7,189,884 B2 | 3/2007 | Mukhopadhyay |
| 7,226,567 B1 | 6/2007 | Olbert |
| 7,282,120 B2 | 10/2007 | Braun |
| 7,297,814 B2 | 11/2007 | Yada et al. |
| 7,345,209 B2 | 3/2008 | Mukhopadhyay |
| 7,371,904 B2 | 5/2008 | Ma et al. |
| 7,378,559 B2 | 5/2008 | Verwijs |
| 7,396,965 B2 | 7/2008 | Mukhopadhyay |
| 7,511,101 B2 | 3/2009 | Nguyen |
| 7,521,029 B2 | 4/2009 | Guetlhuber |
| 7,588,739 B2 | 9/2009 | Sugiyama |
| 7,659,434 B2 | 2/2010 | Mukhopadhyay |
| 7,674,939 B2 | 3/2010 | Mukhopadhyay |
| 7,687,670 B2 | 3/2010 | Nappa |
| 7,695,695 B2 | 4/2010 | Shin |
| 7,714,177 B2 | 5/2010 | Mukhopadhyay |
| 7,836,941 B2 | 11/2010 | Song |
| 7,880,040 B2 | 2/2011 | Mukhopadhyay |
| 7,951,982 B2 | 5/2011 | Mukhopadhyay |
| 8,058,486 B2 | 11/2011 | Merkel et al. |
| 8,058,490 B2 | 11/2011 | Strebelle |
| 8,071,825 B2 | 12/2011 | Johnson et al. |
| 8,071,826 B2 | 12/2011 | Van Der Puy |
| 8,076,521 B2 | 12/2011 | Elsheikh |
| 8,084,653 B2 | 12/2011 | Tung |
| 8,115,038 B2 | 2/2012 | Wilson |
| 8,123,398 B2 | 2/2012 | Teshima |
| 8,158,836 B2 | 4/2012 | Pigamo |
| 8,232,435 B2 | 7/2012 | Sievert |
| 8,258,353 B2 | 9/2012 | Tirtowidjojo |
| 8,258,355 B2 | 9/2012 | Merkel |
| 8,357,828 B2 | 1/2013 | Okamoto et al. |
| 8,367,867 B2 | 2/2013 | Zardi et al. |
| 8,383,867 B2 | 2/2013 | Mukhopadhyay |
| 8,395,000 B2 | 3/2013 | Mukhopadhyay |
| 8,398,882 B2 | 3/2013 | Rao |
| 8,487,146 B2 | 7/2013 | Wilson |
| 8,558,041 B2 | 10/2013 | Tirtowidjojo et al. |
| 8,581,011 B2 | 11/2013 | Tirtowidjojo et al. |
| 8,581,012 B2 | 11/2013 | Tirtowidjojo et al. |
| 8,614,361 B2 | 12/2013 | Suzuki |
| 8,614,363 B2 | 12/2013 | Wilson et al. |
| 8,907,148 B2 | 12/2014 | Tirtowidjojo et al. |
| 8,912,371 B2 * | 12/2014 | Hosaka ............... C07C 17/06 570/227 |
| 8,926,918 B2 | 1/2015 | Tirtowidjojo et al. |
| 8,933,280 B2 | 1/2015 | Tirtowidjojo et al. |
| 8,957,258 B2 | 2/2015 | Okamoto et al. |
| 9,056,808 B2 | 6/2015 | Tirtowidjojo et al. |
| 9,067,855 B2 | 6/2015 | Grandbois et al. |
| 2001/0018962 A1 | 9/2001 | Joshi et al. |
| 2002/0087039 A1 | 7/2002 | Tung et al. |
| 2002/0110711 A1 | 8/2002 | Boneberg et al. |
| 2005/0245774 A1 | 11/2005 | Mukhopadhyay et al. |
| 2006/0150445 A1 | 7/2006 | Redding |
| 2006/0292046 A1 | 12/2006 | Fruchey |
| 2007/0197841 A1 | 8/2007 | Mukhopadhyay |
| 2007/0197842 A1 | 8/2007 | Tung |
| 2007/0265368 A1 | 11/2007 | Rao et al. |
| 2008/0021229 A1 | 1/2008 | Maughon |
| 2008/0073063 A1 | 3/2008 | Clavenna et al. |
| 2008/0118018 A1 | 5/2008 | Schrauwen |
| 2008/0207962 A1 | 8/2008 | Rao |
| 2009/0018377 A1 | 1/2009 | Boyce |
| 2009/0030249 A1 | 1/2009 | Merkel et al. |
| 2009/0088547 A1 | 4/2009 | Schamschurin et al. |
| 2009/0099396 A1 | 4/2009 | Mukhopadhyay |
| 2009/0117014 A1 | 5/2009 | Carpenter |
| 2009/0203945 A1 | 8/2009 | Mukhopadhyay |
| 2009/0253946 A1 | 10/2009 | Van Der Puy |
| 2009/0270568 A1 | 10/2009 | Strebelle et al. |
| 2010/0041864 A1 | 2/2010 | Kadowaki et al. |
| 2010/0185029 A1 | 7/2010 | Elsheikh |
| 2010/0263278 A1 | 10/2010 | Kowoll et al. |
| 2011/0087056 A1 | 4/2011 | Tirtowidjojo et al. |
| 2011/0155942 A1 | 6/2011 | Pigamo et al. |
| 2011/0172472 A1 | 7/2011 | Sakyu |
| 2011/0218369 A1 | 9/2011 | Elsheikh et al. |
| 2011/0251425 A1 | 10/2011 | Penzel |
| 2012/0065434 A1 | 3/2012 | Nose |
| 2014/0081055 A1 | 3/2014 | Tirtowidjojo |
| 2014/0163266 A1 | 6/2014 | Tirtowidjojo et al. |
| 2014/0179962 A1 | 6/2014 | Tirtowidjojo et al. |
| 2014/0323775 A1 | 10/2014 | Grandbois et al. |
| 2014/0323776 A1 | 10/2014 | Grandbois et al. |
| 2014/0336425 A1 | 11/2014 | Tirtowdjojo et al. |
| 2014/0336431 A1 | 11/2014 | Tirtowidjojo et al. |
| 2014/0371494 A1 | 12/2014 | Tirtowidjojo et al. |
| 2015/0045592 A1 | 2/2015 | Grandbois et al. |
| 2015/0057471 A1 | 2/2015 | Tirtowidjojo et al. |
| 2015/0217256 A1 | 8/2015 | Tirtowidjojo et al. |

FOREIGN PATENT DOCUMENTS

| | | |
|---|---|---|
| CN | 101492341 | 7/2009 |
| CN | 101544535 | 9/2009 |
| CN | 101597209 | 12/2009 |
| CN | 101754941 | 6/2010 |
| CN | 101913979 | 12/2010 |
| CN | 101913980 | 12/2010 |
| CN | 101955414 | 1/2011 |
| CN | 101982227 | 3/2011 |
| CN | 102001911 | 4/2011 |
| CN | 102249846 | 11/2011 |
| CN | 102351637 | 2/2012 |
| CN | 1035621264 A | 2/2014 |
| DE | 857955 | 12/1952 |
| DE | 209184 | 4/1984 |
| DE | 235631 | 5/1986 |
| DE | 102005044501 | 3/2007 |
| DE | 102010022414 | 12/2011 |

(56) References Cited

FOREIGN PATENT DOCUMENTS

| | | |
|---|---|---|
| EP | 0131560 | 1/1985 |
| EP | 0164798 | 12/1985 |
| EP | 0453818 | 10/1991 |
| EP | 1018366 | 12/2000 |
| EP | 1097984 | 5/2001 |
| FR | 1546709 | 11/1968 |
| GB | 471186 | 8/1937 |
| GB | 471187 | 8/1937 |
| GB | 471188 | 8/1937 |
| GB | 857086 | 12/1960 |
| GB | 1134585 | 11/1968 |
| GB | 1381619 | 1/1975 |
| GB | 1548277 | 7/1979 |
| JP | 54079207 | 6/1979 |
| JP | S54-135712 | 10/1979 |
| JP | 08-119885 | 5/1996 |
| JP | 2001213820 | 8/2001 |
| JP | 2006272267 | 10/2006 |
| JP | 2007021396 | 2/2007 |
| JP | 2008063314 | 3/2008 |
| JP | 2007-535561 | 5/2008 |
| JP | 2009000592 | 1/2009 |
| JP | 2009046653 | 3/2009 |
| JP | 2001151708 | 6/2011 |
| JP | 2011144148 | 7/2011 |
| LU | 52247 | 12/1966 |
| SU | 899523 | 1/1982 |
| WO | 0138271 | 5/2001 |
| WO | 0138275 | 5/2001 |
| WO | 2005016509 | 2/2005 |
| WO | 2007079431 | 7/2007 |
| WO | 2007079435 | 7/2007 |
| WO | 2007096383 | 8/2007 |
| WO | 2008054781 | 5/2008 |
| WO | 2009015304 | 1/2009 |
| WO | 2009067571 | 5/2009 |
| WO | 2009087423 | 7/2009 |
| WO | 2011060211 | 5/2011 |
| WO | 2011065574 | 6/2011 |
| WO | 2012011844 | 1/2012 |
| WO | 2012081482 | 12/2012 |
| WO | 2012166393 | 12/2012 |
| WO | 2012166394 A1 | 12/2012 |
| WO | 2013082410 | 6/2013 |
| WO | 2014046970 | 3/2014 |
| WO | 2014046977 | 3/2014 |
| WO | 2014066083 | 5/2014 |
| WO | 2014100039 | 6/2014 |
| WO | 2014100066 | 6/2014 |
| WO | 2014134233 | 9/2014 |
| WO | 2014134377 | 9/2014 |
| WO | 2014164368 | 10/2014 |

OTHER PUBLICATIONS

Fields, et al., "Thermal Isomerization of 1,1-dichlorocyclopropanes", Chemical Communications, Jan. 1, 1967, p. 1081, 21.

Galitzenstein, et al., "The Dehydrochlorination of Propylene Dichloride", Journal of the Society of Chemical Industry, 1950, pp. 298-304, 69.

Gault, et al., "Chlorination of Chloroform", Comptes Rendus Des Seances De L'Academie des Sciences, 1924, pp. 467-469, 179.

Gerding, et al., "Raman Spectra of aliphatic chlorine compounds: chloroethenes an chloropropenes", Recueil Jan. 1, 1955, pp. 957-975, 74.

Hatch, et al., "Allylic Chlorides. XV. Preparation and Properties of the 1,2,3Trichloropropenes", JACS, Jan. 5, 1952, pp. 123-126, 74.

Hatch, et al., "Allylic Chlorides. XVIII. Preparation and Properties of 1,1,3-tricholoro-2-fluoro-1-propene and 1,1,2,3- tetrachloro-1-propene", JACS, Jul. 5, 1952, pp. 3328-3330, 74(13).

Herzfelder, "Substitution in the Aliphatic Series", Berichte Der Deutschen Chemischen Gesellschaft, May-Aug. 1893, pp. 1257-1261, 26(2).

Huaping, et al., "Procress in Synthesis of 1,1,1,3-tetrachloropropane", Guangzhou Chemicals, 2011, , pp. 41-42, 39(5).

Ivanov, et al., "Metal phthalocyanine-Catalyzed Addition of polychlorine-Containing Organic Compounds to C=C Bonds", Russian Chemical Bulletin, International Edition, Nov. 2009, pp. 2393-2396, 58(11).

Kang, et al., "Kinetics of Synthesis of 1,1,1,3,3-pentachlorobutane Catalyzed by Fe—FeCl3", Chemical Research and Application, Jun. 2011, pp. 657-660, 23(6).

Kharasch, et al., "Chlorinations with Sulfuryl Chloride.I. The Peroxide-Catalyzed Chlorination of Hydrocarbons", JACS, 1939, pp. 2142-2150, 61.

Khusnutdinov, et al., "CCl4 Attachment to Olefins Catalyzed by Chromium and Ruthenium Complexes. Impact of Water as a Nucleophilic Admixture", Oil Chemistry, 2009, pp. 349-356, vol. 4.

Kruper, et al., "Synthesis of alpha-Halocinnamate Esters via Solvolytic Rearrangement of Trichloroallyl Alcohols", J Org Chem, 1991, pp. 3323-3329, 56.

Leitch, "Organic Deuterium Compounds: V. The chlorination of propyne and propyne D-4", Canadian Journal of Chemistry, Apr. 1, 1953, pp. 385-386, 30(4).

Levanova, et al., "Cholorination of Chloroolefins C3—C4", Doklady Chemistry, vol. 386, No. 4, 2002, 496-498.

Levanova, et al., "Thermocatalytic Reactions of Bromochloropropanes", Russian Journal of Physical Chemistry, Jan. 1, 1983, pp. 1142-1146, 57.

McBee, et al., "Utilization of Polychloropropanes and Hexachloroethane", Industrial and Engineering Chemistry, Feb. 1, 1941, pp. 176-181, 33(2).

Mouneyrat, "Effect of Chlorine on Propyl Chloride in the Presence of Anhydrous Aluminum Chloride", Bulletin de la Societe chimique de france, Societe francaise de chimie, Jan. 1, 1899, pp. 616-623, 21(3).

Munoz-Molina, et al., "An Efficient, Selective and Reducing Agent-Free Copper Catalyst for the Atom-Transfer Radical Addition of Halo Compounds to Activated Olefins", Inorg. Chem., 2010, pp. 643-645, 49.

Nair, et al., "Atom Transfer Radical Addition (ATRA) of Carbon Tetrachloride and Chlorinated Esters to Various Olefins Catalyzed by CP/Ru(PPh3)(PR3)Cl Complexes", Inorganica Chimica Acta, 2012, pp. 96-103, 380.

Nguyen, et al., "Condensation de chloroforme avec des olefins fluorees en milieu basique", Journal of Fluorine Chemistry, Dec. 1, 1991, pp. 241-248, 55(3).

Nikishin, et al., "Reactions of Methanol and Ethanol with Tetrachloroethylene", Izvestiya Akademii Nauk SSSR, Seriya Khimicheskaya, Dec. 1966, pp. 2188-2192, 12.

Ochi, et al., "Preparation of Chloropropenes by Photochemical Dehydrochlorination of 1,2-Dichloropropane", Chemical Abstracts, Jul. 17, 1989, p. 574, 111(3).

Pozdnev, et al., "Chlorination of chloroform and the conversion of methylene chloride manufacture still residues", Khim., Khim. Tekhnol., 1970, 70(4).

Rotshtein, et al., "Isomer Distribution on Chlorination of Chloropropanes", Z. Organicheskoi Khimii, 1966, pp. 1539-1542, 2(9).

Semenov, "Selectivity of Photochemical Chlorination of Chloromethane in the Liquid Phase", Prikladnei Khimii, 1985, pp. 840-845, 58(4).

Shelton, et al., "Addition of Halogens and Halogen Compounds to Allylic Chlorides. I. Addition of Hydrogen Halides", Journal of Organic Chemistry, 1958, pp. 1876-1880, 23.

Skell, et al., "Reactions of BrCl with alkyl radicals", Tetrahedron letters, 1986 pp. 5181-5184, 27(43).

Skell, et al., "Selectivities of pi and sigma succinimidyl radicals in substitution and addition reactions, Response to Walling, Wl-Taliawi and Zhao", JACS, Jul. 1, 1983, pp. 5125-5131, 105(15).

Stevens, "Some New Cyclopropanes with a Note on the Exterior Valence Angles of Cyclopropane", JACS, Vo. 68, No. 4, 1945, 620-622.

(56) References Cited

OTHER PUBLICATIONS

Tanuma, et al., "Partially Fluorinated Metal Oxide Catalysts for a Friedel-Crafts-type Reaction of Dichlorofluoromethane with Tetrafluoroethylene", Catal. Lett, 2010, pp. 77-82, 136.
Tobey, et al., "Pentachlorocyclopropane", Journal of the American Chemical Society, Jun. 1, 1996, pp. 2478-2481, 88 (11).
Urry, et al., "Free Radical Reactions of Diazomethane with Reactive Bromopolychloroalkane", JACS, May 5, 1964, pp. 1815-1819.
Wang Chin-Hsien, "Elimination Reactions of polyhalopropanes under emulsion catalytic conditions to give Halopropenes", Synthesis, Jan. 1, 1982, pp. 494-496, 1982(6).
Zhao, et al., "Research Progress on Preparation Technology of 1,1,2,3-Tetrachloropropene", Zhejiang Chemical Industry, 2010, pp. 8-10, 41(6).
Zheng, et al., "Preparation of the low GWP alternative 1,3,3,3-tetrafluoropropene", Zhejiang Huagong, 2010, pp. 5-7, 41(3).

* cited by examiner

PROCESS FOR THE PRODUCTION OF CHLORINATED PROPENES

This application is a 371 of PCT/US2013/075863, filed Dec. 17, 2013 which claims benefit of 61/739,341, filed Dec. 19, 2012.

FIELD

The present invention relates to processes for the production of chlorinated propenes.

BACKGROUND

Hydrofluorocarbon (HFC) products are widely utilized in many applications, including refrigeration, air conditioning, foam expansion, and as propellants for aerosol products including medical aerosol devices. Although HFC's have proven to be more climate friendly than the chlorofluorocarbon and hydrochlorofluorocarbon products that they replaced, it has now been discovered that they exhibit an appreciable global warming potential (GWP).

The search for more acceptable alternatives to current fluorocarbon products has led to the emergence of hydrofluoroolefin (HFO) products. Relative to their predecessors, HFOs are expected to exert less impact on the atmosphere in the form of a lesser or non-detrimental impact on the ozone layer and their much lower GWP as compared to HFC's. Advantageously, HFOs also exhibit low flammability and low toxicity.

As the environmental, and thus, economic importance of HFO's has developed, so has the demand for precursors utilized in their production. Many desirable HFO compounds, e.g., such as 2,3,3,3-tetrafluoroprop-1-ene or 1,3,3,3-tetrafluoroprop-l-ene, may typically be produced utilizing feedstocks of chlorocarbons, and in particular, chlorinated propenes, which may also find use as feedstocks for the manufacture of polyurethane blowing agents, biocides and polymers.

Unfortunately, many chlorinated propenes may have limited commercial availability, and/or may only be available at prohibitively high cost, due at least in part to the complicated, multi-step processes typically utilized in their manufacture. This may be due at least in part to the fact that conventional processes for their manufacture may require the use of starting materials that are prohibitively expensive to be economically produced by manufacturers on the large scale required to be useful as feedstocks. Although more cost effective starting materials are known, their use can result in the production of larger quantities of less desirable intermediates than conventional starting materials. And so, the cost savings initially provided may be spent dealing with the removal or disposal of these undesirable intermediates.

It would thus be desirable to provide improved processes for the production of chlorocarbon precursors useful as feedstocks in the synthesis of refrigerants and other commercial products. More particularly, such processes would provide an improvement over the current state of the art if they were less costly in starting materials, while also providing for the use of secondary products rather than requiring additional processing costs for removal of the same.

BRIEF DESCRIPTION

The present invention provides efficient processes for the production of chlorinated propenes. Advantageously, the processes make use of 1,2-dichloropropane, a by-product in the production of chlorohydrin, as a low cost starting material, alone or in combination with 1,2,3-trichloropropane. Although advantageous at least for the cost savings it provides, the use of dichloropropane as a starting material can tend to result in the production of large quantities of 1,1,1,2,2-pentachloropropane, which is not readily processed to the desired final product. It has now been discovered that, while 1,1,1,2,2-pentachloropropane is not readily dehydrochlorinated via conventional techniques to provide, e.g., 1,1,2,3-tetrachloropropene, it can be efficiently dehydrochlorinated using suitable catalysts to provide the desired final product, rendering the use of PDC as a starting material even more economically feasible.

In one aspect, the present invention provides a process for the production of chlorinated propenes from a feedstream comprising 1,2-dichloropropane. The process comprises the catalytic dehydrochlorination of at least a portion of the pentachloropropanes produced by the chlorination of the PDC feedstream. In some embodiments, the pentachloropropanes comprise 1,1,1,2,2-pentachloropropane. The dehydrochlorination catalyst is selected from the group consisting of aluminum chloride, antimony pentachloride, titanium tetrachloride, or a combination of these. In some embodiments, at least one of these may be used in combination with ferric chloride. Desirably, the dehydrochlorination catalyst is utilized in amounts of less than 5 mole %, or even less than 2 mole %, of the total reaction mixture. Additional dehydrochlorinations may be carried out, and in such embodiments, may be carried out in the liquid phase, in the presence of a chemical base. Because at least one catalytic dehydrochlorination step is utilized, the recovery of HCl as a byproduct is possible.

DETAILED DESCRIPTION

The present specification provides certain definitions and methods to better define the present invention and to guide those of ordinary skill in the art in the practice of the present invention. Provision, or lack of the provision, of a definition for a particular term or phrase is not meant to imply any particular importance, or lack thereof. Rather, and unless otherwise noted, terms are to be understood according to conventional usage by those of ordinary skill in the relevant art.

The terms "first", "second", and the like, as used herein do not denote any order, quantity, or importance, but rather are used to distinguish one element from another. Also, the terms "a" and "an" do not denote a limitation of quantity, but rather denote the presence of at least one of the referenced item, and the terms "front", "back", "bottom", and/or "top", unless otherwise noted, are merely used for convenience of description, and are not limited to any one position or spatial orientation.

If ranges are disclosed, the endpoints of all ranges directed to the same component or property are inclusive and independently combinable (e.g., ranges of "up to 25 wt. %, or, more specifically, 5 wt. % to 20 wt. %," is inclusive of the endpoints and all intermediate values of the ranges of "5 wt. % to 25 wt. %," etc.). As used herein, percent (%) conversion is meant to indicate change in molar or mass flow of reactant in a reactor in ratio to the incoming flow, while percent (%) selectivity means the change in molar flow rate of product in a reactor in ratio to the change of molar flow rate of a reactant.

Reference throughout the specification to "one embodiment" or "an embodiment" means that a particular feature, structure, or characteristic described in connection with an embodiment is included in at least one embodiment. Thus, the appearance of the phrases "in one embodiment" or "in an embodiment" in various places throughout the specification is not necessarily referring to the same embodiment. Further, the particular features, structures or characteristics may be combined in any suitable manner in one or more embodiments.

In some instances, "PDC" may be used as an abbreviation for 1,2-dichloropropane, "TCP" may be used as an abbreviation for 1,2,3-trichloropropane and "TCPE" may be used as an abbreviation for 1,1,2,3-tetrachloropropene. The terms "cracking" and "dehydrochlorination" are used interchangeably to refer to the same type of reaction, i.e., one resulting in the creation of a double bond typically via the removal of a hydrogen and a chlorine atom from adjacent carbon atoms in chlorinated hydrocarbon reagents.

The present invention provides efficient processes for the production of chlorinated propenes from a feedstream comprising PDC. The use of PDC, a byproduct in many chlorohydrin and allyl chloride processes, as a starting material is economically more attractive than disposing of it via incineration, as may be done in connection with some conventional chlorohydrin and allyl chloride processes.

The chlorination of PDC can lead to the production of large amounts of 1,1,1,2,2-pentachloropropane, in addition to other pentachloropropane isomers. Unlike other pentachloropropane isomers, however, 1,1,1,2,2-pentachloropropane cannot be readily dehydrochlorinated using caustic to produce 1,1,2,3-tetrachloropropene. As a result, processes using PDC as a starting material may exhibit lower yields than desired, or economically feasible, to 1,1,2,3-tetrachloropropene.

It has now been discovered that 1,1,1,2,2-pentachloropropane dehydrochlorinates readily in the presence of certain catalysts to provide 1,1,2,3-tetrachloropropene. And so, in the present process, at least a portion of the pentachloropropanes produced by the process is catalytically cracked using a catalyst selected from the group consisting of aluminum chloride, antimony pentachloride, titanium tetrachloride, or combinations of these.

It has now been surprisingly discovered that these catalysts are not only capable of cracking 1,1,1,2,2-pentachloropropane, but also, that when so doing, the more desirable isomer, 1,1,2,3-tetrachloropropene, is provided almost exclusively. This is especially surprising since those of ordinary skill would expect cracking 1,1,1,2,2-pentachloropropane to predominantly produce 2,3,3,3-tetrachloropropene. Although it is expected that some amount of 2,3,3,3-tetrachloropropene is produced using the present process, it is believed that that under the cracking conditions utilized, at least a portion, if not substantially all, of any such amount isomerizes to provide 1,1,2,3-tetrachloropropene. This result is surprising since 1,1,1,2,2-pentachloropropane does not crack in response to conventional caustic cracking conditions, and even more surprising since ferric chloride, also a Lewis acid, is not effective to crack 1,1,1,2,2-pentachloropropane.

Any other dehydrochlorinations utilized in the process may occur in either the gas or liquid phase, and may occur in the presence of a chemical base, or catalyst in the case of additional gas phase dehydrochlorinations. In some embodiments of the present processes, one or more additional gaseous catalytic dehydrochlorinations are utilized, in addition to the initial gaseous dehydrochlorination of PDC, and as a result, such processes may provide a further reduction of caustic cracking steps as compared to conventional processes. In such embodiments, additional amounts anhydrous HCl can be recovered. Anhydrous HCl is of greater value than the sodium chloride that would be produced as byproduct(s) if conventional caustic cracking steps were utilized. The present process thus results in the production of a by-product that may either be sold or used as a feedstock for other processes, e.g., ethylene oxyhalogenation to produce ethylene dichloride. If the use of catalysts is desired, suitable dehydrochlorination catalysts include, but are not limited to, aluminum chloride ($AlCl_3$), antimony pentachloride ($SbCl_5$), titanium tetrachloride ($TiCl_4$), ferric chloride ($FeCl_3$), or combinations of these, may be used.

In other embodiments, additional dehydrochlorination steps of the present process may be conducted in the presence of a chemical base or liquid caustic. Many chemical bases are known in the art to be useful for this purpose, and any of these can be used. For example, suitable bases include, but are not limited to, alkali metal hydroxides, such as sodium hydroxide, potassium hydroxide, calcium hydroxide; alkali metal carbonates such as sodium carbonate; lithium, rubidium, and cesium or combinations of these. Phase transfer catalysts such as quaternary ammonium and quaternary phosphonium salts can also be added to improve the dehydrochlorination reaction rate with these chemical bases.

Any chlorinations utilized in the process may be conducted in the liquid phase with or without the use of catalysts, however, catalysts can be used if desired, to enhance the present process. For example, free radical initiators are suitable for use, and those of ordinary skill in the art are aware of many. Known free radical catalysts or initiators are desirably used to enhance the present process. Such catalysts may typically comprise one or more chlorine, peroxide or azo- (R—N=N—R') groups and/or exhibit reactor phase mobility/activity. As used herein, the phrase "reactor phase mobility/activity" means that a substantial amount of the catalyst or initiator is available for generating free radicals of sufficient energy which can initiate and propagate effective turnover of the product, the chlorinated and/or fluorinated propene(s), within the design limitations of the reactor.

Furthermore, the free radical initiator should have sufficient homolytic dissociation energies such that the theoretical maximum of free radicals is generated from a given initiator under the temperature/residence time of the process. It is especially useful to use free radical initiators at concentrations where free radical chlorination of incipient radicals is prevented due to low concentration or reactivity. Surprisingly, the utilization of the same, does not result in an increase in the production of impurities by the process, but does provide selectivities to the chlorinated propenes of at least 50%, or up to 60%, up to 70%, and in some embodiments, up to 80% or even higher.

Such free radical initiators are well known to those skilled in the art and have been reviewed, e.g., in "Aspects of some initiation and propagation processes," Bamford, Clement H. Univ. Liverpool, Liverpool, UK., Pure and Applied Chemistry, (1967), 15(3-4),333-48 and Sheppard, C. S.; Mageli, O. L. "Peroxides and peroxy compounds, organic," Kirk-Othmer Encycl. Chem. Technol., 3rd Ed. (1982), 17, 27-90.

Taking the above into consideration, examples of suitable free radical initiators comprising chlorine include, but are not limited to carbon tetrachloride, hexachloroacetone, chloroform, hexachloroethane, phosgene, thionyl chloride, sulfuryl chloride, trichloromethylbenzene, perchlorinated alkylaryl functional groups, or organic and inorganic hypochlorites, including hypochlorous acid, and t-butylhypochlorite, methylhypochlorite, chlorinated amines (chloramine) and chlorinated amides or sulfonamides such as chloroamine-T®, and the like. Examples of suitable free radical initiators comprising one or more peroxide groups include hydrogen peroxide, hypochlorous acid, aliphatic and aromatic peroxides or hydroperoxides, including di-t-butyl peroxide, benzoyl peroxide, cumyl peroxide and the like. Diperoxides offer an advantage of being able to propagate competitive processes (e.g., the free radical chlorination of PDC to TCP (and its isomers) and tetrachloropropanes). In addition, compounds, such as azobisisobutyronitrile (AIBN) or 1,1'-azobis(cyclohexanecarbonitrile (ABCN), may have utility in effecting the chlorination of PDC to trichloropropanes and tetrachloropropanes under the conditions of this invention. Combinations of any of these may also be utilized.

The chlorination reactor may be subjected to pulse laser or continuous UV/visible light sources at a wavelength suitable for inducing photolysis of the free radical catalyst/initiator, as taught by Breslow, R. in *Organic Reaction Mechanisms* W.A. Benjamin Pub, New York p 223-224. Wavelengths from 300 to 700 nm of the light source are sufficient to dissociate commercially available radical initiators. Such light sources include, .e.g., Hanovia UV discharge lamps, sunlamps or even pulsed laser beams of appropriate wavelength or energy which are configured to irradiate the reactor chamber. Alternatively, chloropropyl radicals may be generated from microwave discharge into a bromochloromethane feedsource introduced to the reactor as taught by Bailleux et al., in Journal of Molecular Spectroscopy, 2005, vol. 229, pp. 140-144.

Ionic chlorination catalysts may also be used to catalyze the chlorinations performed in the present process. Ionic chlorination catalysts remove a chlorine and hydrogen from adjacent carbon atoms, the adjacent carbon atoms form a double bond, and HCl is released. A chlorine molecule is then added back, replacing the double bond, to provide a more highly chlorinated alkane. Ionic chlorination catalysts are well known to those or ordinary art and any of these may be used in the present process. Exemplary ionic chlorination catalysts include, but are not limited to, aluminum chloride, ferric chloride ($FeCl_3$) and other iron containing compounds, iodine, sulfur, antimony pentachloride ($SbCl_5$), boron trichloride ($BCl_3$), lanthanum halides, metal triflates, and combinations thereof Any or all of the catalysts utilized in the process can be provided either in bulk or in connection with a substrate, such as activated carbon, graphite, silica, alumina, zeolites, fluorinated graphite and fluorinated alumina. Whatever the desired catalyst (if any), or format thereof, those of ordinary skill in the art are well aware of methods of determining the appropriate format and method of introduction thereof. For example, many catalysts are typically introduced into the reactor zone as a separate feed, or in solution with other reactants.

The amount of any free radical chlorination and/or dehydrochlorination catalyst utilized will depend upon the particular catalyst chosen as well as the other reaction conditions. Generally speaking, in those embodiments of the invention wherein the utilization of a catalyst is desired, enough of the catalyst should be utilized to provide some improvement to reaction process conditions (e.g., a reduction in required temperature) or realized products, but yet not be more than will provide any additional benefit, if only for reasons of economic practicality.

For purposes of illustration only then, it is expected that useful concentrations of a free radical initiator or ionic chlorination catalyst will range from 1 ppm to 20% by weight, or from 10 ppm to 10%, or from 0.01% to 5 wt. % If a dehydrochlorination catalyst is utilized for one or more dehydrochlorination steps, useful concentrations may range from 0.01 wt. % to 5 wt. %, or from 0.05 wt. % to 2 wt. % at temperatures of 70° C. to 200° C. If a chemical base is utilized for one or more dehydrochlorinations, useful concentrations of these will range from 0.01 to 20 grmole/L, or from 0.1 grmole/L to 15grmole/L, or from 1 grmole/L to 10 grmole/L, inclusive of all subranges there between. Relative concentrations of each catalyst/base are given relative to the feed, e.g. 1,2-dichloropropane alone or in combination with 1,2,3-trichloropropane.

The chlorination steps of the process may be carried out using any chlorination agent, and several of these are known in the art. For example, suitable chlorination agents include, but are not limited to chlorine, and/or sulfuryl chloride ($SO_2Cl_2$). Combinations of chlorinating agents may also be used. Either or both $Cl_2$ and sulfuryl chloride may be particularly effective when aided by the use of the aforementioned ionic chlorination catalysts.

The present process can make use of one or more chlorinated alkanes to produce the desired chlorinated propenes. Desirably, the one or more chlorinated alkanes comprise 1,2-dichloropropane, which may be available at low cost due to its production as a by-product in many chlorohydrin and allyl chloride processes. The process feedstock may also comprise trichloropropane, or other chlorinated alkanes, if desired. And, the one or more chlorinated alkanes may be generated within or upstream of the process, if desired, e.g., as a byproduct in a chlorohydrin process, or by any other methods known to those of ordinary skill in the art.

Any chlorinated propene may be produced using the present method, although those with 3-4 chlorine atoms are more commercially sought after, and production of the same may thus be preferred in some embodiments. In some embodiments, the process may be used in the production of 1,1,2,3-tetrachloropropene, which is highly sought after as a feedstock for refrigerants, polymers, biocides, etc.

In additional embodiments, one or more reaction conditions of the process may be optimized, in order to provide even further advantages, i.e., improvements in selectivity, conversion or production of reaction by-products. In certain embodiments, multiple reaction conditions are optimized and even further improvements in selectivity, conversion and production of reaction by-products produced can be seen.

Reaction conditions of the process that may be optimized include any reaction condition conveniently adjusted, e.g., that may be adjusted via utilization of equipment and/or materials already present in the manufacturing footprint, or that may be obtained at low resource cost. Examples of such conditions may include, but are not limited to, adjustments to temperature, pressure, flow rates, molar ratios of reactants, mechanical mixing, etc.

That being said, the particular conditions employed at each step described herein are not critical, and are readily determined by those of ordinary skill in the art. What is important is that PDC is utilized as a starting material, and that at least a portion of the pentachloropropanes generated by the process are catalytically dehydrochlorinated using a dehydrochlorination catalyst selected from the group consisting of aluminum chloride, antimony pentachloride, titanium tetrachloride, or combinations of these. Those of ordinary skill in the art will readily be able to determine suitable equipment for each step, as well as the particular conditions at which the chlorination, dehydrochlorination, separation, drying, and isomerization steps may be conducted.

In one exemplary embodiment, PDC is fed to a liquid phase reactor, e.g., such as a batch or continuous stirred tank autoclave reactor with an internal cooling coil. A shell and multitube exchanger followed by vapor liquid disengagement tank or vessel can also be used. Suitable reaction conditions include, e.g., temperatures of from ambient temperature (e.g., 20° C.) to 200° C., or from 30° C. to 150° C., or from 40° C. to 120° C. or from 50° C. to 100° C. Ambient pressure may be used, or pressures of from 100 kPa to 1000 kPa, or from 100 kPa to 500 kPa, or from 100 kPa to 300 kPa. At such conditions, and using one or more ionic chlorination catalysts, PDC is chlorinated to tri-, tetra-, and pentachlorinated propanes at conversions of greater than 60%, or 70%, or 80%, or 85%, or 90% or 95%, or even up to 100% can be seen.

The process may be carried out neat, i.e., in the absence of solvent, or, one or more solvents may be provided to the chlorination reactor, and may be provided as feedstock, or, recycled from one or more separation columns operably disposed to receive streams from the chlorination reactor. For example, monochloropropene intermediates may be recycled back to the chlorination reactor from one separation column, tri-and tetrachloropropane intermediates may be recycled from another separation column and/or the chlorination reactor may be provided with a feedstock of any appropriate solvent for chlorination reactions, such as, e.g., carbon tetrachloride, sulfuryl chloride, 1,1,2,3,3-pentachloropropane, 1,1,2,2,3,3-hexachloropropane, other hexachloropropane isomers, or other suitable aqueous or alcohol based solvents, or a combination of these.

The overhead vapor from the chlorination reactor, is cooled, condensed and fed to a first separation column. This column is operated at conditions effective to provide anhydrous HCl to an overhead line thereof and chlorine through a bottom recycle line.

More particularly, the top temperature of such a column can typically be set below 0° C. or more preferably, can be set at a temperature of from −70° C. to −10° C. The bottom temperature of this column is desirably set at from 10° C. to 150° C., or from 30° C. to 100° C., with the exact temperature dependent to some degree on the bottom mixture composition. The pressure of this column is desirably set above 200 kPa or preferably, from 500 kPA to 2000 kPa, or more preferably from 500 kPa to 1000 kPa. The bottom stream of a column operated at such conditions would be expected to contain excess chlorine, unreacted PDC and monochloropropene intermediates, while the overhead stream would be expected to comprise anhydrous HCl.

The liquid product stream from the chlorination reactor may be fed to a second separation column operated at conditions effective to separate the tri- and tetra-chlorinated propanes from the pentachlorinated propanes. The overhead stream from this separation column, comprising tri- and tetra-chlorinated propanes, may be recycled back to the chlorination reactor for further conversion/chlorination, while the bottom stream, expected to comprise pentachloropropanes and heavier by-products, such as isomers of hexachloropropanes, may be provided to a further separation column.

This third separation column separates the desirable pentachloropropanes, i.e., 1,1,2,2,3-pentachloropropane, 1,1,1,2,3-pentachloropropane, and 1,1,1,2,2-pentachloropropane, from the less desirable 1,1,2,3,3-pentachloropropane and heavier components, which are purged as a bottom stream.

The overhead stream comprising 1,1,2,2,3-pentachloropropane, 1,1,1,2,3-pentachloropropane, and 1,1,1,2,2-pentachloropropane is then provided to a catalytic dehydrochlorination reactor where it is catalytically dehydrochlorinated in the presence of a catalyst selected from the group consisting of aluminum chloride, antimony pentachloride, titanium tetrachloride, or combinations of these, to provide 2,3,3,3-tetrachloropropene and 1,1,2,3-tetrachloropropene. In some embodiments, the catalytic dehydrochlorination catalyst may further comprise ferric chloride.

This catalytic dehydrochlorination reactor may typically be a batch or a continuous stirred tank reactor. The mixing can be done, e.g., by mechanical stirrer, static mixer or jet mixing of feed streams. The reactor is equipped with an internal or external heat exchanger to maintain reaction temperature from 60° C. to 120° C. or preferably from 70° C. to 100° C. or more preferably from 80° C. to 90° C. The overhead of the reactor can be equipped with a condenser operated at below 50° C. to remove anhydrous HCl and return the organic reactant and products. The reactor can be operated at or above ambient pressure so as to efficiently remove HCl byproduct.

The liquid product stream from this catalytic dehydrochlorination reactor is expected to comprise 1,1,2,3-tetrachloropropane as well as unreacted pentachloropropane isomers, i.e., those substantially unaffected by the catalytic dehydrochlorination reaction conditions. More particularly, it is expected that this stream will comprise 1,1,2,3-tetrachloropropene, 1,1,2,2,3-pentachloropropane, small amounts of unconverted 1,1,1,2,2- and 1,1,1,2,3-pentachloropropanes and dissolved HCl. This product stream may then be fed to a further dehydrochlorination unit, desirably one conducted with liquid base or caustic without first removing the product TCPE. Advantageously, the use of a caustic cracking step here can also serve to quench the Lewis acid catalyst as presence of the same during a distillation step can result in the decomposition of chlorinated organics in the reboiler.

The reaction stream from the caustic dehydrochlorination reactor may optionally be provided to a drying unit, and the dried stream therefrom provided to a further distillation unit to recover the TCPE product and its isomer in the overhead stream and unreacted chloropropanes intermediate in the bottom streams. The bottom stream is then recycled to a separation unit where the pentachloropropanes intermediate is recovered and recycled to the catalytic dehydrochlorination reactor.

Separated TCPE and its isomer may then be fed to a reactor to isomerize the 2,3,3,3-tetrachloropropene to 1,1,2,3-tetrachloropropene under the appropriate conditions. For example, catalysts may be utilized to assist in the isomerization, in which case, suitable catalysts include, but are not limited to (i) siliceous granules having a polar surface including kaolinite, bentonite, and attapulgite; (ii) other mineral salts of silica such as saponite or quartz; or (iii) siliceous non-mineral substance such as silica gel, fumed silica, and glass, or combinations of any of these. Suitable conditions for drying columns for such reaction streams are also known to those of ordinary skill in the art, as evidenced by U.S. Pat. No. 3,926,758.

Figure 1:
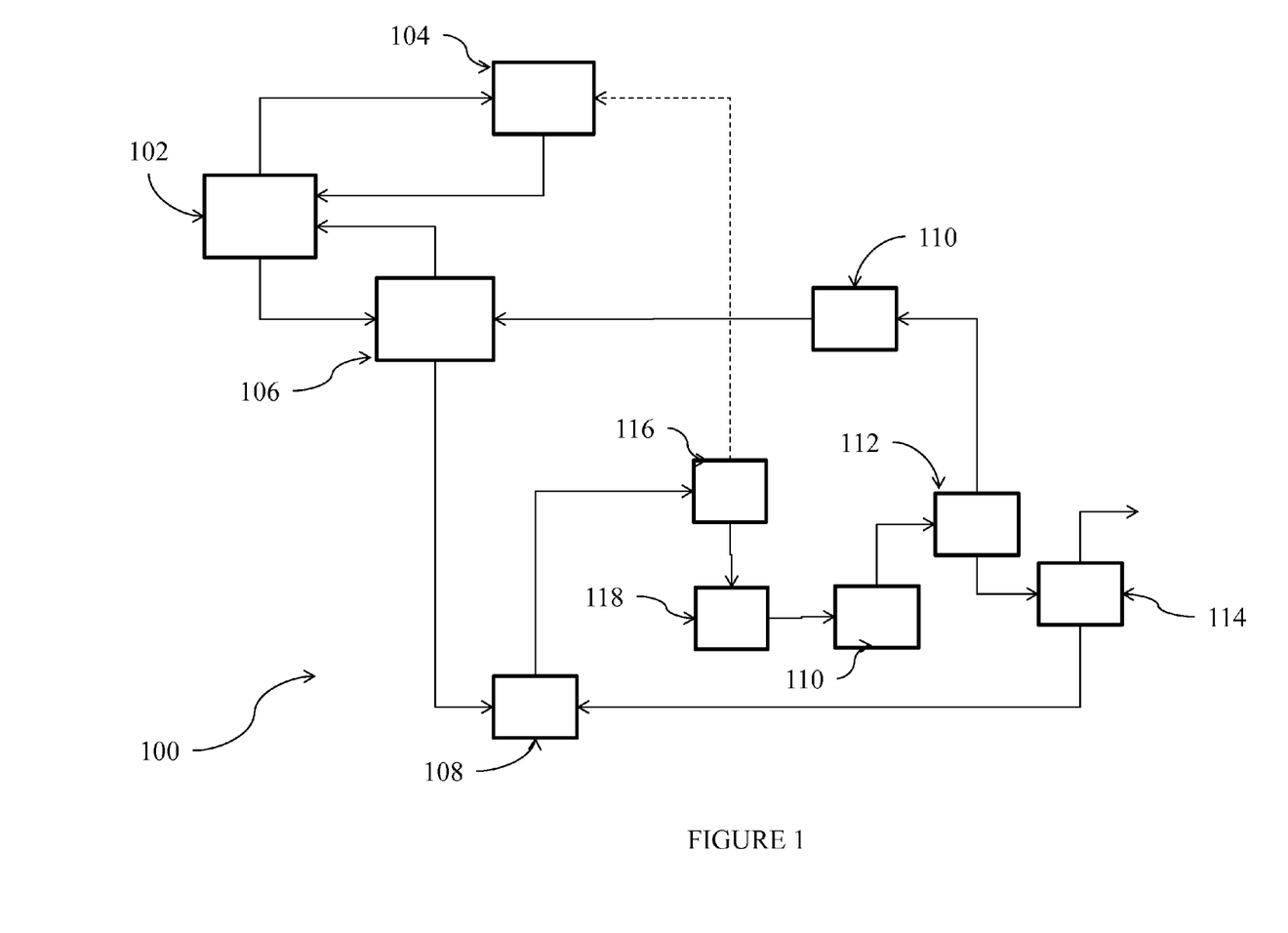
FIG. 1 shows a schematic representation of a process according to one embodiment.

A schematic illustration of such a process is shown in FIG. 1. As shown in FIG. 1, process 100 would make use of chlorination reactors 102, 120, separation units 104, 106, 108, 112, and 114, dehydrochlorination reactors 116 and 118 and drying unit 110.

In operation, the feed to chlorination reactor 102 comprises fresh PDC, and recycled trichloropropanes, one or more chlorinating agents, and optionally, one or more initiators or catalysts. Chlorination reactor 102 is operated at conditions provide an overhead stream comprising anhydrous HCl, and unreacted chlorine and PDC, and a bottoms stream comprising unreacted PDC and chlorinated propane products comprising 3-6 chlorine atoms. The overhead stream is provided to separation column 104, for the separation and recovery of anhydrous HCl. Separation column 104 provides a bottoms stream comprising unreacted PDC and chlorine which may be recycled to chlorination reactor 102.

The bottoms stream from chlorination reactor 102 is provided to separation unit 106, operated at conditions effective to provide an overhead stream comprising PDC and trichloropropane and tetrachloropropane intermediates which may be recycled to chlorination reactor 102, and a bottoms stream comprising 1,1,2,3-tetrachloropropane, pentachloropropanes and heavier secondary products which is provided to separation unit 108.

Separation unit 108 separates the 1,1,2,3-tetrachloropropane and desirable pentachloropropanes from the undesirable pentachloropropane isomer, 1,1,2,3,3-pentachloropropane, and hexachloropropanes, which may be appropriately disposed of The desirable pentachloropropanes are provided overhead to catalytic dehydrochlorination reactor 116 and dehydrochlorinated to provide 1,1,2,3-tetrachloropropene (TCPE).

More specifically, the overhead stream from separation unit 108 may desirably comprise 1,1,2,3-tetrachloropropene, and 1,1,2,2,3-, 1,1,1,2,3- and 1,1,1,2,2,-pentachloropropane. Although 1,1,1,2,2,-pentachloropropane in particular does not crack under normal caustic cracking conditions to produce 1,1,2,3-tetrachloropropene, this isomer will catalytically crack using aluminum chloride, antimony chloride, titanium chloride, combinations of these, or combinations of any of these with ferric chloride to provide TCPE. To do so, dehydrochlorination reactor 116 is desirably operated at temperatures of 80° C.-100° C., pressures of atmospheric or higher, with catalyst concentrations of 2 wt % or greater.

Catalytic dehydrochlorination reactor 116 advantageously produces a stream of HCl, which may be provided to separation unit 104 for the recovery of further amounts of anhydrous HCl. The product stream from catalytic dehydrochlorination reactor 116, expected to comprise 1,1,2,3-tetrachloropropane, 1,1,2,3-tetrachloropropene, and 1,1,2,2,3-pentachloropropane, is provided directly to dehydrochlorination reactor 118, which may desirably be a caustic dehydrochlorination reactor, wherein the 1,1,2,3-tetrachloropropane, and 1,1,2,2,3-pentachloropropane are caustic cracked to produce a product stream comprising TCPE and trichloropropenes. Optionally, the product stream from reactor 116 may be provided to a quench unit (not shown) to remove AlCl3 before being fed to dehydrochlorination reactor 118. The product stream from dehydrochlorination reactor 118 is fed to drying unit 110 to remove water and water soluble secondary products, such as aluminum hydroxide and sodium chloride. This stream is then fed to a separation unit 112 which provides trichloropropene as an overhead stream and TCPE and unreacted 1,1,2,3-tetrachloropropane and pentachloropropane as the bottom stream.

The overhead stream of 112 comprising trichloropropenes is fed to a liquid phase chlorination reactor 120 where they are converted to a product stream comprising pentachloropropane intermediates and unreacted chlorine. The product stream is then recycled to separation unit 106 to recover the pentachloropropane intermediates and chlorine which is recycled to chlorination reactor 102.

The bottom stream of separation unit 112 comprising TCPE and unreacted 1123-tetrachloropropane and pentachloropropanes is then fed to separation unit 114 to recover TCPE as the overhead stream. The bottoms stream of 114, comprising unreacted pentachloropropanes and 1,1,2,3-tetrachloropropane is recycled to separation unit 108.

Figure 2:
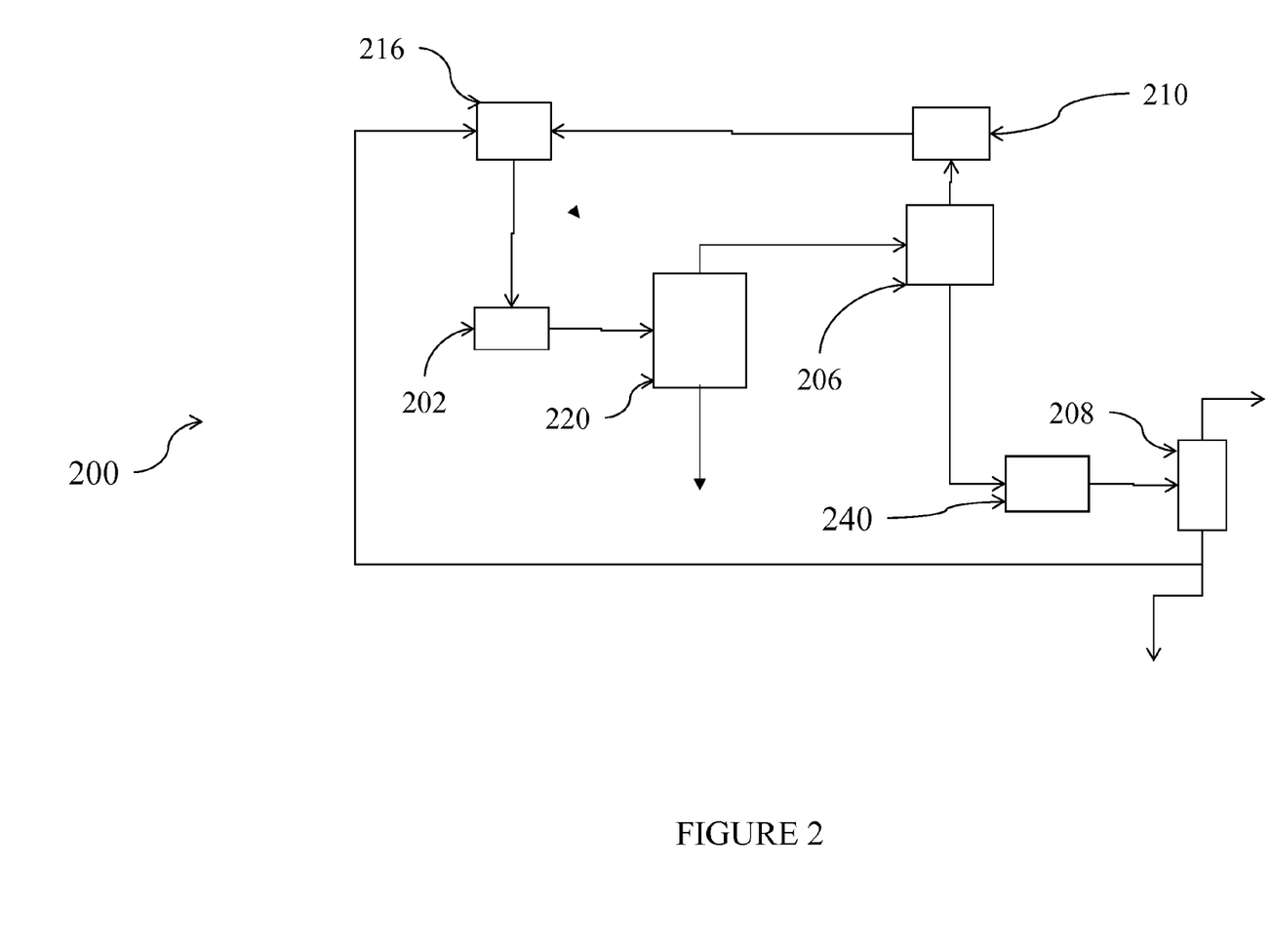
FIG. 2 shows a schematic representation of a process according to another embodiment.

An additional exemplary process is shown in FIG. 2. As shown in FIG. 2, process 200 would make use of dehydrochlorination reactors 202 and 216, drying unit 220, separation units 206 and 208, chlorination reactor 210, isomerization reactor 240. Whereas process 100 begins with a chlorination step, process 200 begins with a dehydrochlorination step.

In operation, the feed to dehydrochlorination reactor 202 contains fresh PDC, and recycled PDC, tri-, tetra-, and pentachloropropanes and di-, tri-, and tetrachloropropenes together with 50 wt % caustic soda solution. Dehydrochlorination reactor 202 is desirably operated at conditions sufficient to produce the corresponding mono-, di-, tri- and tetrachloropropenes.

The crude product, along with any unconverted PDC and recycled chloropropanes, is sent to drying unit 220 to remove water and water soluble secondary products, such aluminum hydroxide and sodium chloride in a bottoms stream. The organic product from drying unit 220 is provided to separation unit 206. In some embodiments, drying unit 220 may comprise multiple columns (not shown), e.g., a heterogeneous azeotropic distillation could be carried out by using a drying column and a water removal column. In such embodiments, the overhead streams of both columns would be combined in a decanter (not shown), with the water phase fed to the water column (not shown) and the organic phase fed to the drying column (not shown).

The separation unit 206 is operated at below atmospheric pressure and with a reboiler temperature lower than the boiling point of TCPE (167° C.) such that the overhead stream thereof comprises organics lighter than TCPE, e.g., monochloropropenes, dichloropropenes, and trichloropropenes and unreacted chloropropanes. This overhead stream is then fed to liquid phase chlorination reactor 210 to convert the mono, di, and trichloropropenes to tri, tetra, and pentachloropropanes, respectively. This product stream of chlorination reactor 210 is provided to catalytic dehydrochlorination reactor 216. The product stream from catalytic dehydrochlorination reactor 216 is advantageously provided to caustic dehydrochlorination reactor 202, which can also act to crack any catalyst present in the product stream from catalytic dehydrochlorination reactor 216.

The bottom stream of separation unit 206, comprising 1,1,2,3-TCPE and its isomer 2,3,3,3-tetrachloropropene, can be provided to isomerization reactor 240 to convert 2,3,3,3-tetrachloropropene to 1,1,2,3-TCPE. The product of isomerization reactor 240 is fed to the separation unit 208 to recover TCPE as the overhead product. The bottom stream of separation unit 208 comprises unreacted tetra- and pentachloropropanes, as well as heavier byproducts. This stream can be purged to prevent the heavies from accumulating in the system, or, the tetrachloropropane and pentachloropropane can be separated from this stream by the use of an additional separation column (not shown) before being recycled back to dehydrochlorination reactor 216. Optionally, anhydrous HCl in the overhead stream of 216 can be removed and purified for use in other process.

For process 200, all dehydrochlorination reactions, e.g., of PDC, TCP, tetrachloropropanes, and pentachloropropanes, etc., are carried out in two liquid phase dehydrochlorination reactors. Advantageously, the product stream from the catalytic dehydrochlorination unit is provided to the caustic dehydrochlorination unit, where the chemical base and/or caustic solution may act to quench at least a portion of any catalyst in the product stream from the catalytic dehydrochlorination reactor. This reduces, or even eliminates, the potential for the catalyst to catalyze unwanted reactions in downstream equipment. As a result, the use of a quench unit between catalytic dehydrochlorination unit 216 and the next process step can be avoided, and capital cost savings are provided.

The chlorinated and/or fluorinated propenes produced by the present process may typically be processed to provide further downstream products including hydrofluoroolefins, such as, for example, 1,3,3,3-tetrafluoroprop-1-ene (HFO-1234ze). Since the present invention provides an improved process for the production of chlorinated propenes, it is contemplated that the improvements provided will carry forward to provide improvements to these downstream processes and/or products. Improved methods for the production of hydrofluoroolefins, e.g., such as 2,3,3,3-tetrafluoroprop-1-ene (HFO-1234yf), are thus also provided herein.

The conversion of chlorinated and/or fluorinated propenes to provide hydrofluoroolefins may broadly comprise a single reaction or two or more reactions involving fluorination of a compound of the formula $C(X)_mCCl(Y)_n(C)(X)_m$ to at least one compound of the formula $CF_3CF=CHZ$, where each X, Y and Z is independently H, F, Cl, I or Br, each m is independently 1, 2 or 3 and n is 0 or 1. A more specific example might involve a multi-step process wherein a feedstock of a chlorinated and/or fluorinated propene is fluorinated in a catalyzed, gas phase reaction to form a compound such as 1-chloro-3,3,3-trifluoropropene (1233zd). The 1-chloro-3,3,3-trifluoropropene (1233zd) is hydro fluorinated to provide 1-chloro-2,3,3,3-tetrafluoropropane that is then dehydrochlorinated to 1,3,3,3-tetrafluoropropene via a catalyzed, gas phase reaction.

In the following examples, individual chloropropane isomers are identified by reference to the positions of the chlorine atoms, i.e., 112 indicates 1,1,2-trichloropropane, 1123 indicates 1,1,2,3-tetrachloropropane, 11223 indicates 1,1,2,2,3-pentachloropropane, and so on. For chlorinated propenes, similar nomenclature is used, with an "e" added as a suffix, e.g., 112e indicates 1,1,2-trichloropropene, 1123e indicates 1,1,2,3-tetrachloropropene, 11223e indicates 1,1,2,2,3-pentachloropropene, and so on.

Example 1

A neat mixture of 1,1,1,2,2-pentachloropropane and 1,1,2,2,3-pentachloropropane is caustic cracked using 5N NaOH and a catalytic amount of the phase transfer catalyst tetrabutylammonium chloride at 50° C. The mixture is stirred vigorously at this temperature for an hour and sampled. Stirring is continued overnight at the same conditions.

Figure 3:
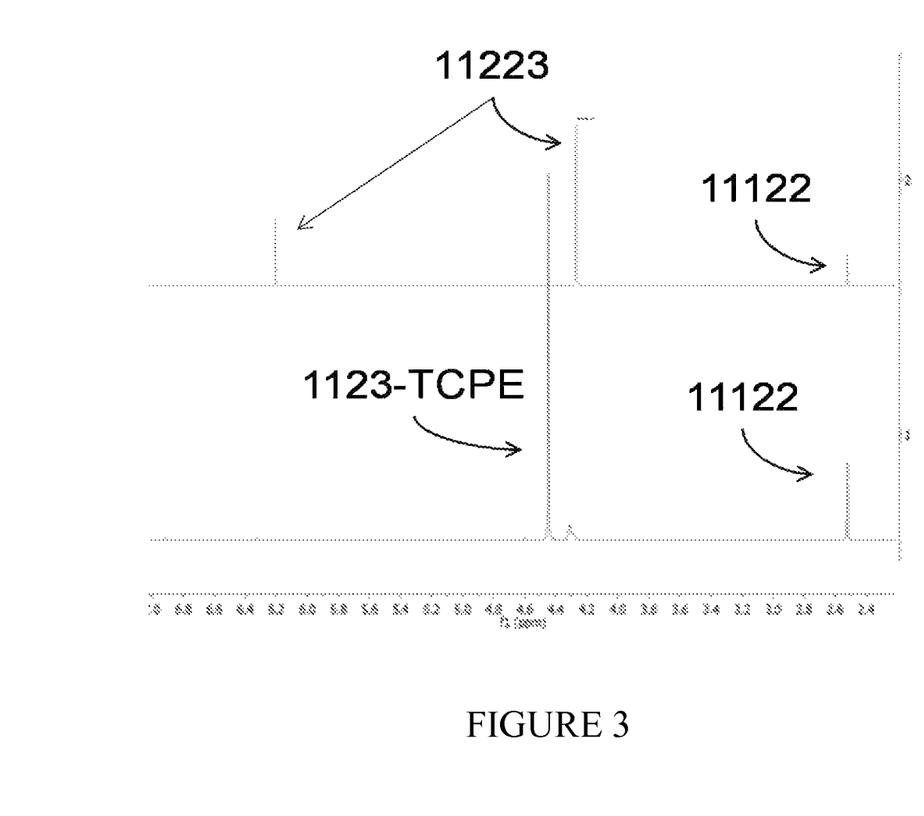
FIG. 3 shows an NMR spectrum of a product stream according to one embodiment.

After 1 hour, all of the 1,1,2,2,3-pentachloropropane is converted to 1,1,2,3-tetrachloropropene while essentially none of the 1,1,1,2,2-pentachloropropane had been consumed. After overnight stirring, a large amount of the 1,1,1,2,2-pentachloropropane remains unconsumed as shown by the NMR spectrum in FIG. 3.

Example 2

Figure 4:
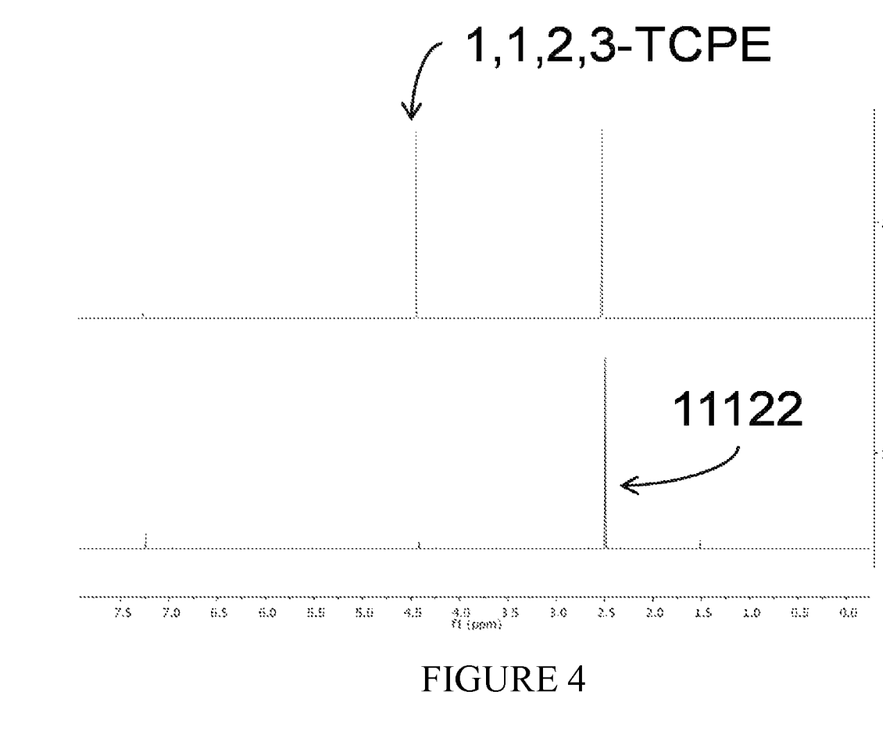
FIG. 4 shows an NMR spectrum of the feedstream (bottom) and a product stream (top) according to another embodiment.

A solution of 1,1,1,2,2-pentachlorpropane in carbon tetrachloride is dehydrochlorinated using $AlCl_3$ as the catalyst. At 80° C., 1,1,1,2,2-pentachloropropane is to TCPE as shown in the product (top) NMR spectrum provided at FIG. 4. The starting material spectrum is the bottom spectrum in FIG. 4. While the anticipated product of this reaction is 2,3,3,3-TCPE, it is believed that 2,3,3,3-TCPE rearranges under these conditions to provide 1,1,2,3-TCPE as the predominant product. Taken together, Examples 1 and 2 show that, while 1,1,1,2,2 does not dehydrochlorinate in response to caustic cracking conditions, 1,1,1,2,2-pentachloropropane not only cracks when contacted with the Lewis acid catalyst aluminum chloride, but also surprisingly provides the desired TCPE isomer, 1,1,2,3 almost exclusively.

Example 3

The dehydrochlorination of 1,1,1,2,2-pentachloropropane is attempted using FeCl3 as a catalyst, with all other conditions being identical to those of Example 2, i.e., carbon tetrachloride is utilized as a solvent and the reaction is carried out at 80 C. 1,1,1,2,2-pentachloropropane is unreactive at these conditions, undergoing essentially no (<5% conversion) to either 2,3,3,3-TCPE or 1,1,2,3-TCPE. Taken in combination with Example 2, this Example shows that while ferric chloride is completely ineffective at catalytically cracking 1,1,1,2,2-pentachloropropane, aluminum chloride is not only effective, but the conditions at which it may be used surprisingly result in the provision of 1,1,2,3-TCPE almost exclusively.

The invention claimed is:

1. A process for the production of 1,1,2,3-tetrachloropropene from a feedstream comprising 1,2-dichloropropane, wherein the 1,2-dichloropropane is converted to one or more pentachloropropanes, wherein at least a portion of the pentachloropropanes produced by the process are catalytically dehydrochlorinated using at least one dehydrochlorination catalyst selected from the group consisting of aluminum chloride, antimony pentachloride, titanium tetrachloride, and a combination of these, wherein the pentachloropropanes comprise 1,1,1,2,2-pentachloropropane, and wherein the catalytic dehydrochlorination produces a stream comprising 1,1,2,3-tetrachloropropene and unreacted pentachloropropanes.

2. he process of claim 1, wherein the total concentration of dehydrochlorination catalyst is less than 5 mole % of the total reaction mixture.

3. The process of claim 1, further comprising at least one additional liquid phase dehydrochlorination conducted in the presence of chemical base.

4. The process of claim 3, wherein the feedstream from the catalytic dehydrochlorination is provided to the liquid phase dehydrochlorination.

5. The process of claim 1, wherein the catalyst is quenched by the product of the chemical base dehydrochlorination and removed from the product stream.

6. The process of claim 1, wherein the feedstream further comprises 1,2,3-trichloropropane.

7. The process of claim 1, wherein HCl is generated as byproduct(s).

8. The process of claim 7, wherein HCl is recovered as anhydrous HCl.

9. The process of claim 3, wherein the chemical base comprises caustic, potasium hydroxide, calcium hydroxide or a combination of these.

10. The process of claim 1, wherein the product stream is quenched to reduce the dehydrochlorination catalyst.

11. The process of claim 10 wherein the quenched catalyst is removed from the product stream.

* * * * *